United States Patent [19]

Burton et al.

[11] Patent Number: 4,626,513

[45] Date of Patent: Dec. 2, 1986

[54] METHOD AND APPARATUS FOR LIGAND DETECTION

[75] Inventors: James A. Burton, Amesbury; Bernard Hoop, Jr., Wakefield, both of Mass.

[73] Assignee: Massachusetts General Hospital, Boston, Mass.

[21] Appl. No.: 550,400

[22] Filed: Nov. 10, 1983

[51] Int. Cl.⁴ ................ G01N 33/543; G01N 33/544; G01N 33/542

[52] U.S. Cl. .................... 436/518; 436/535; 436/537; 436/807; 436/804; 436/56; 436/57; 436/172; 436/178; 436/531; 422/58; 422/68

[58] Field of Search ............ 436/514, 518, 531, 537, 436/535, 507, 56, 57, 172, 178; 424/1.1; 128/654, 659; 422/58, 68

[56] References Cited

U.S. PATENT DOCUMENTS

| | | | |
|---|---|---|---|
| 3,010,908 | 11/1961 | Broderick et al. | 436/57 |
| 3,976,763 | 8/1976 | Spector | 424/1.5 |
| 4,000,252 | 12/1976 | Kosak | 424/1 |
| 4,035,155 | 7/1977 | Durie et al. | 23/230.3 |
| 4,181,853 | 1/1980 | Abu-Shumays et al. | 436/172 |
| 4,256,834 | 3/1981 | Zuk et al. | 436/537 |
| 4,264,330 | 4/1981 | Schmidt et al. | 436/56 |
| 4,271,139 | 6/1981 | Hart | 424/1 |
| 4,293,436 | 10/1981 | Fost | 436/57 |
| 4,382,074 | 5/1983 | Hart | 436/537 |
| 4,399,099 | 8/1983 | Buckles | 436/514 |

Primary Examiner—Christine M. Nucker
Attorney, Agent, or Firm—Lahive & Cockfield

[57] ABSTRACT

A process and apparatus has been developed for radioassay of ligand in solution which eliminates the separation step required in conventional techniques. A chamber is provided containing a quenching solution, a plurality of ligand molecules and a plurality of receptor molecules. One of pluralities forms a free species labelled with a beta particle emitter while the other is immobilized on a solid support, e.g., the chamber wall or a microbead, within the chamber. Ligand introduced with the sample competes with ligand molecules already in the chamber for receptor sites on the receptor molecules and the free species is allowed to diffuse about the chamber. A beta particle detector in communication with the chamber at a fixed position detects only those beta particles emitted from within the quenching distance of the quenching solution. The quenching properties of the solution are used in place of the conventional separation step. The process and apparatus are easily adapted for continuous monitoring of ligand level and are particularly well suited for use in radioimmunoassays. The apparatus can be miniturized allowing implantation in an animal body and in vivo monitoring of ligand level in bodily fluids.

38 Claims, 9 Drawing Figures

METHOD AND APPARATUS FOR LIGAND DETECTION

BACKGROUND OF THE INVENTION

The present invention relates to the detection of ligand in solution. More particularly, the invention relates to a process and apparatus for performing homogeneous radioassays which do not require the separation step of conventional assays. Elimination of the separation step permits continuous monitoring of ligand level and promotes the possibility of automation of the assay.

Currently, a variety of processes are used to detect low levels of chemical materials or ligand in solution. Radioassays, particularly radioimmunoassays (RIA), are especially useful for biomedical applications because of their sensitivity and excellent reproducibility. RIAs have been developed which detect ligand levels of one nanogram ($10^{-9}$ grams) with a reproducibility of better than one percent. While similar levels of reproducibility have been achieved with other assays, radioassays are the assay of choice because of their sensitivity.

The basis of all radioassays is the specificity of the reaction between a receptor molecule, e.g., an antibody, and the ligand, e.g., an antigen. High specificity means that the receptor will react with the ligand but is substantially unreactive with any other species. Generally, the greater the specificity of the ligand/receptor pair, the greater the sensitivity of the reaction.

While all radioassays depend on the ligand/receptor reaction, a number of radioassay procedures have been used to detect ligand concentration in samples. In every radioassay, there is a labelled or tagged species and an unlabelled species. Labelling or tagging means incorporating a radioactive atom into the molecule either by atomic substitution or by covelant bonding. In some cases, a macromolecule may be linked to a small ligand and the radioactive atom is incorporated into the macromolecule. The procedure chosen for the radioassay depends, in part, on the properties of the ligand of interest. If the ligand is easily tagged with a radioactive atom, competitive procedures whereby untagged ligand in the sample competes for receptor sites with tagged ligand are normally used. If the ligand is difficult to tag, the receptor, e.g., the antibody, may be tagged and the procedure chosen should include means for differentiating between free receptor molecules and ligand/receptor pairs.

Radioassays are further divided into solution assays and solid phase assays. In the solution assays, receptor molecules and ligands react in solution and the separation step differentially precipitates bound pairs from free species. Activated charcoal and ammonium sulfate precipitation are common methods of separating bound from free species in solution. The radioactivity level of either the precipitent or the solution can be counted in order to determine ligand concentration.

Solid phase radioassays were first described by Catt and his co-workers in 1967 (see Catt, et al, Solid Phase Radioimmunoassays; Nature 213: 825-827 (1967)). In solid phase assays, one species of the ligand/receptor pair is bound to a solid support while the other constitutes a free species. The bound member can be adsorbed onto the solid support, e.g., a test tube wall, or covalently bound on the support by a chemical reaction. In either case, a free species tagged with the radioactive atom is allowed to react with the bound member. In conventional techniques, the unreacted, labelled free species is separated from the bound, labelled free species and, preferably, the solid phase is counted for radioactivity. The resulting value normally is compared with a standard curve to determine the concentration of ligand in the sample. Conventional solid phase techniques include single and double antibody immunoassays. In single antibody techniques, the antibody is normally the bound species and labelled antigen competes with unlabelled antigen for the antibody binding sites. In double antibody techniques, antibody is bound to the solid support, labelled antibody is a free species in solution and the ligand forms a bridge or sandwich between bound antibody and labelled antibody.

Conventional radioassays are non-homogenous; that is, they require a separation step in order to function. This separation step is one of the causes of inaccuracy and other difficulties in automation of radioassays. To combat these problems, a number of homogenous assays have been developed using non-radioactive techniques. One such technique is the spin-immunoassay as described by Leute et al, Spinimmunoassay Technique of Opiate Narcotic in Urine and Saliva; J. Am. Med. Assoc., 221: 1231-1234 (1971). In a spinimmunoassay, the ligand is attached to a stable free radical whose concentration is determined by electron spin resonance (esr). Reaction of the spin-labelled ligand with an antibody diminishes the esr reading. The introduction of unlabelled ligand from a sample causes the spin-labelled ligand to be displaced from the antibody, increasing the esr of the solution and indicating the ligand concentration of the sample.

Another homogenous technique is the fluorescence polarization assay described by Haber et al, Polarization of Fluorescence as a Measure of Antigen-Antibody Interaction, Proc. Natl. Acad. Sci., USA 48: 1935-1942 (1962). In fluorescence polarization assays, the free radical bound to ligand in the spin-immunoassay is replaced with a dye that fluoresces only when the ligand is bound by an antibody. Unlabelled ligand reacts with antibody, displacing labelled ligand from the antibody and decreasing the fluorescence of the solution. The decrease in fluorescence is a measure of ligand concentration in the sample.

A further homogenous assay is the EMIT or Enzyme Multiplied Immunoassay Technique described by Bastiani in The EMIT System: A Commercially Successful Innovation; Antibiotics and Chemotherapy 26: 89-97 (1979). The EMIT system has the ligand bound to the enzyme proximate to the enzyme active site. Reaction with a antibody sterically blocks the enzyme activity. Addition of free ligand from the sample displaces antibody from the enzyme/ligand complex, causing an increase in enzyme activity indicative of the ligand concentration in the sample.

ELISA or enzyme linked immunosorbent assay, described by Enquall, et al, in Enzyme-Linked Immunosorbent Assay (ELISA), Quantitative Assay of Immunoglobulin G; Immunochem. 8: 871-879 (1971), is another nonradioassay technique which has been used with success. ELISA is the enzyme counterpart of previously described double antibody technique. Unlabelled antibody is bound to a solid support, e.g., a test tube wall, and reacts with a ligand having at least two reactive sites. The bound ligand binds the second antibody labelled with an enzyme and after a separation step, the bound enzyme concentration, indicative of ligand concentration, is measured.

The major problem with the homogenous enzyme assays is that the sensitivity of radioassays is better than the sensitivity of enzyme assays. Development of a homo-genous radioassay would be a step forward because a number of ligands of interest have very low concentration in biological fluids. It also should be noted that none of the homogenous assays described above is particularly well suited for in vivo ligand detection.

Accordingly, an object of the invention is to produce a homogenous radioassay having excellent sensitivity and reproducibility. Another object of the invention is to provide an apparatus for performing a homogenous radioassay. A further object is to provide a process and apparatus adapted for continous ligand assay. A still further object of the invention is to provide a process and apparatus adapted for in vivo determination of ligand concentration. Another object is to provide a process for ligand detection adaptable for automation. A further object is to provide a radioassay capable of use for ligand detection in a nonequilibrium mode.

These and other objects and features of the invention will be apparent from the following drawing and the description.

SUMMARY OF THE INVENTION

The present invention provides both a process and apparatus useful for radioassay of ligand. The apparatus of the invention is capable of providing continuous ligand assay thereby providing the possibility of automated assay.

The invention features an apparatus for detecting the presence of the ligand in the sample. The apparatus includes a reaction chamber containing a plurality of receptor molecules and a plurality of ligand molecules, one of the pluralities constituting a free species labelled with a beta particle emitting radioactive atom and the other forming a species immobilized on a solid support. The ligand molecules are molecules which can compete with ligand for reactive sites on receptor molecules. The apparatus further includes an associated sensor responsive to incident beta particles from radioactive atoms. The associated sensor, which may be fixed relative to the solid support, generates a signal representative of the incident number of beta particles. The sensor is responsive only to particles disposed within a given region of the chamber; other beta particles emitted from the free species are quenched by a quenching solution, preferably aqueous, within the chamber. This quenching solution, which may include the sample and, possibly, a chamber medium already in the chamber, quenches the beta particles before they travel a predetermined distance D. The apparatus also includes a device for introducing the sample into the chamber, preferably a membrane permeable to ligand and substantially impermeable to ligand molecules. If the membrane is used as the device for introducing the sample into the chamber, the apparatus can be adapted for continuous detection of ligand and beta particles. Preferably, the ligand molecules are the free species and constitute ligand bound to radioactively tagged macromolecules. The apparatus may include a device for delivering an output signal from the associated sensor to a detection apparatus. The apparatus of the invention may be miniturized to form a chamber implantable in an animal body, which is capable of in vivo detection of ligand. For in vivo detection, bodily fluid of the animal traverses the membrane and can be assayed for ligand concentration.

The associated sensor preferably includes a surface of a material which fluoresces in response to incident beta particles. This surface may constitute a wall of the chamber and most preferably, the surface should be the solid support for the immobilized species. The associated sensor may also include a device communicating with the surface for detecting fluorescent events, preferably a scintillation counter. If the receptor molecules constitute the free species, the ligand molecules may be ligand.

The process of the invention features a multi-step radioassay for detecting the presence of ligand in a sample. The process uses a chamber substantially identical to that described above. The ligand molecules and the ligand in the sample compete for attachment sites on the receptor molecules and the free species difuses about the chamber. A signal generated by the associated sensor is compared with a base value to determine whether the ligand is present in the sample.

In various embodiments, either the receptor molecules or the ligand molecules can be immobilized on the solid support within a distance D of the associated sensor while the other plurality constitutes a free species labelled with the radioactive atoms. During the reaction step, a portion of the labelled species difuses away from the associated sensor so that a portion of the beta particles emitted from the free species is quenched by the quenching solution before reaching the sensor. The concentration of ligand in the sample is a monotonically decreasing function of the output signal from the associated sensor.

In alternate embodiments, the plurality of receptor molecules or ligand molecules are immobilized on a solid support at a distance greater than D from the associated sensor while the other plurality constitutes the labelled free species. During the reaction step, a portion of the labelled species difuses away from the immobilized species to location less than D from the associated sensor. A portion of the beta particles emitted from this portion of the free species is detected by the sensor and the concentration of ligand is a monotonically increasing function of the output signal of the sensor. If the receptor molecules are the free species, the ligand molecules can be ligand.

Since the reaction between the ligand molecules and receptor molecules is an equilibrium reaction, a portion of the ligand molecules may react with the receptor molecules prior to the introduction of the sample into the chamber. This may increase assay sensitivity. It should be noted that it is also possible to use the process under nonequilibrium conditions. In the most preferred embodiment of the invention, the receptor molecules are antibodies while the ligand constitutes antigen.

The invention further features an apparatus for continuous assay of an aqueous sample. The apparatus includes a solid support for immobilizing either ligand molecules or receptor molecules disposed within a chamber at the first location. The receptor molecules are capable of reversibly binding with the ligand and the ligand molecules. The apparatus also includes a beta particle detector including a device responsive to incident beta particles which delivers to the exterior of the chamber an output signal indicative to the number of incident beta particles. The beta particle detector is in communication with the chamber at the second location. The apparatus also includes a device for introducing the aqueous sample into the chamber, preferably a semipermeable membrane permeable to ligand and substantially impermeable to ligand molecules. The semipermeable membrane distinguishes between ligand and ligand molecules based on a property such as size or charge. Most preferably, the semipermeable membrane forms a portion of a wall of the chamber. The aqueous sample includes a solution capable of quenching a beta particle before the particle travels a predetermined distance D within the solution. The distance between the first and second locations can either be less than or greater than this predetermined distance D. Preferably, the device responsive to beta particles includes a surface of a material which fluoresces in response to incident beta particles. The preferred beta particle detector includes an optical fiber for communicating the signal from the fluorescent surface to a scintillation counter. The chamber can be made sufficiently small to be implantable in an animal body to provide a continuous in vivo assay to ligand concentration in the body fluid.

DESCRIPTION

Figure 1:
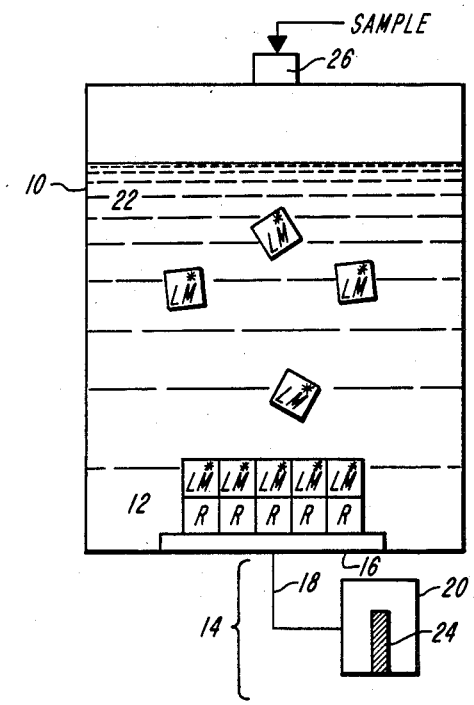
FIG. 1 is a schematic diagram of an apparatus of the invention at a time $t_0$ before introduction of the ligand. The apparatus has the receptor molecules R as the immobilized species bound to a wall of the chamber at a distance less than the quenching distance D from the beta particle detector. A portion of the labelled ligand molecules LM* are illustrated as bound to the receptor molecules.

The present invention provides a process and apparatus capable of performing radioassays, e.g., RIAs, on a continuous basis. The invention is based, in part, on recognition that the quenching properties of solutions can be used to differentiate between bound and free labelled molecules thereby permitting elimination of the separation step required by conventional radioassays. Elimination of the separation step allows the radioassay to be used for determining ligand levels of continually changing samples, e.g., blood. Automation of the assay is easier since all tests are performed on homogenous samples.

As previously noted, radioassays are based on the specificity of the ligand/receptor reaction. The more sensitive radioassays have receptors with substantially similar specificity for ligand and ligand molecules. Since the ligand and ligand molecules compete for attachment sites on receptor molecules, the concentration of ligand in solution is a function of the number of radioactive particles incident on the detector. As long as the amount of ligand in solution is approximately equal to the amount of ligand molecules, the concentration of ligand in the unknown is a monotonic function of the detector output.

Radioactive atoms useful for radioassays emit primarily gamma and beta particles. While a number of radioassays use gamma emitters, e.g., $^{125}$I, as the radioactive atom, the energy of many gamma particles is too high for use in the present invention because the quenching distance of the gamma particles in aqueous solutions is too great. However, beta particles emitted by radioactive atoms normally have lower energy and can be quenched by aqueous solutions within reasonable distances, normally on the order of one milimeter. Table I illustrates the maximum energy, the maximum range and the geometric efficiencies at various distances for the two beta emitters most commonly used in RIAs, tritium and carbon-14.

TABLE I

| Radio-nucleide | $E_m$(MeV) | $R_m$($10^{-6}$ m) | $E_g$ (100 angstroms) | $E_g$ ($10^7$ angstroms) |
|---|---|---|---|---|
| $^3$H | 0.0816 | 15 | 0.23 | 0.00 |
| $^{14}$C | 0.156 | 40 | 0.30 | 0.00 |

The maximum energy ($E_m$) is the end point or highest energy of the energy spectrum of emitted particles from the radioactive atom and is normally measured in MeV. The maximum range ($r_m$) is the maximum distance that a beta particle of energy $E_m$ will travel in an aqueous solution. This value is illustrated in micrometers ($10^{-6}$m or $10^4$ angstroms). The geometric efficiency ($E_g$) is the fraction of the emitted beta particles having energy $E_m$ that will reach a detector from the given distance in an aqueous medium.

As may be seen from Table I, 23% of the beta particles emitted by tritium ($^3$H) and 30% of the beta particles emitted by carbon-14 ($^{14}$C) will reach a detector from 100 angstroms while substantially no particles will travel $10^7$ angstroms (1 mm) in the same medium. In other words, 70-77% of the emitted particles are quenched by passage through 100 angstroms of aqueous medium while a 1 mm passage quenches substantially all of the particles. The 100 angstroms distance is chosen since the radioactive atom of a reacting ligand molecule/receptor molecule pair is constrained to be the within 100 angstroms of the detector surface if one of the pair is bound to the surface. If the radioactive atom-containing free species does not react with the immobilized species, the unreacted free species will diffuse about the chamber until an equilibrium distribution is reached. At the equilibrium distribution, only a small portion of the unreacted free species will be within 1 mm of the detector so if the immobilized species is bound to the surface adjacent the detector, substantially all of the particles incident on the detector will be from the immobilized species. On the other hand, if the immobilized species is bound at a distance greater than the quenching distance from the detector, only the particles emitted by radioactive atoms within the quenching distance will reach the detector. In this manner, the quenching of the beta particles by aqueous solutions allows elimination of the separation step required in conventional radioassays.

The figures described herein are purely illustrative and are intended merely to assist in showing the efficacy of the invention. These figures are schematics and no attempt has been made to show the chamber to scale.

Figure 2:
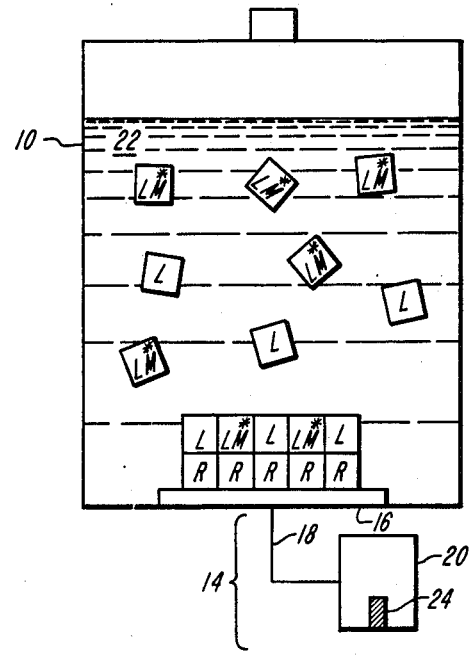
FIG. 2 illustrates the same system as FIG. 1 at a time $t_2$ after introduction of the ligand.

FIG. 1 and 2 illustrate the same system at two different times; FIG. 1 illustrates the system at $t_0$ before introduction of the sample containing ligand L, while FIG. 2 illustrates the apparatus at time $t_2$ after ligand L has competed with the radioactive labelled ligand molecules LM* for binding sites on the receptor molecules R. Specifically, the receptor molecules R form an immobilized species bound to a wall 12 of the chamber 10 adjacent to the beta particle detecting means 14. Detecting means 14 consists of fluorescent surface 16, optical fiber 18 and scintillation chamber 20. Incident beta particles from bound ligand molecules LM* strike surface 16 which fluoresces and the light emitted by the fluorescent event is transmitted by optical fiber 18 to scintillation counter 20 where an electrical output signal is generated. At time $t_0$ (FIG. 1), some ligand molecules LM* are a free species in aqueous solution 22 but the majority of the ligand molecules LM* are bound to receptor molecules R. The star (*) indicates that the molecules contain the radioactive atom. Reading 24 on counter 20 is high in FIG. 1 because the bound ligand molecules are within about 100 angstroms of surface 16 so a large portion of the beta molecules emitted are not quenched by solution 22 and are incident on fluorescent surface 16.

A sample containing ligand L is introduced into chamber 10 through a sample input port 26 at a time $t_1 (t_0 < t_1 < t_2)$ and displaces a portion of ligand molecules LM* from the bonding sites on receptor molecules R. The reaction between the receptor molecules R and the ligand L or ligand molecule LM* is an equilibrium reaction so the amount of bound ligand and bound ligand molecules are functions of their concentrations. It is assumed that the specificity, i.e., the equilibrium constant, for the ligand/receptor and ligand molecule/receptor pairs is approximately equal; however, by comparing the output values from scintillation counter 20 with the standard curve made by serial dilution of a known ligand sample, the ligand concentration of the unknown can be determined even if there is a disparity in specificity.

FIG. 2, illustrating a time $t_2$ after introduction of the sample, shows there is competition for binding sites on receptor molecules R between ligand L and ligand molecules LM*. A portion of the ligand molecules LM* is displaced from the binding sites on receptor molecules R and diffuses away from fluorescent surface 16. The beta particles emitted by these ligand molecules LM* are quenched by solution 22 leading to a reduction in fluorescent events at fluorescent surface 16 and thereby a reduction in reading 24.

Figure 5:
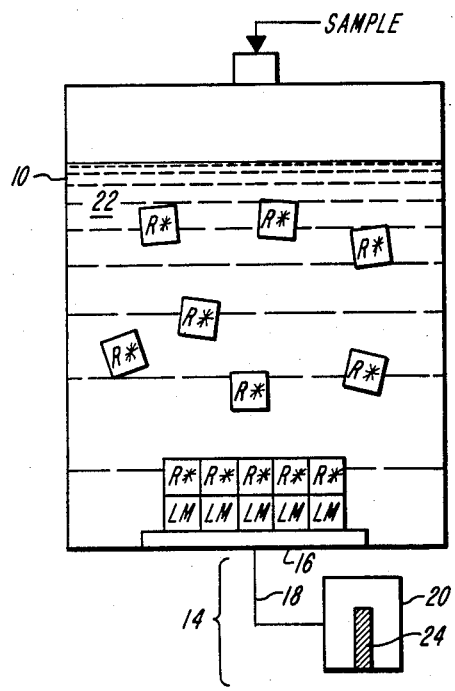
FIG. 5 illustrates an apparatus identical to that of FIG. 1 at time $t_0$ except the receptor molecules R are immobilized at a position greater quenching than distance D from the beta particle detector.
Figure 6:
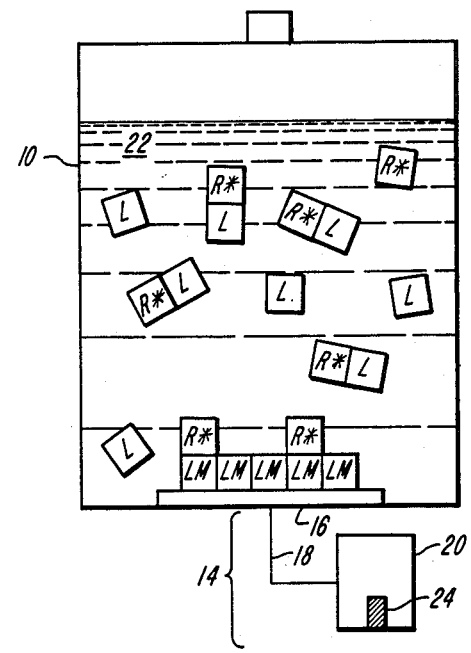
FIG. 6 illustrates the same system as FIG. 5 at time $t_2$.

FIGS. 5 and 6 represent a similar apparatus except the receptor molecules R* are the free species labelled with the radioactive atoms and the ligand molecules LM are the species immobilized on wall 16 adjacent to fluorescent surface 16. At time $t_0$, (FIG. 5), the majority of the receptor molecules R* are bound to the ligand molecules LM adjacent to fluorescent surface 16. At time $t_2$ (FIG. 6), a number of receptor molecules R* are stripped from the ligand molecules LM and react with ligand L in solution. A portion of the R*/L pairs diffuses away from surface 16 and the number of beta particles incident on surface 16 decreases leading to a decrease in fluorescent events at surface 16 as reflected by a decrease in reading 24.

Figure 3:
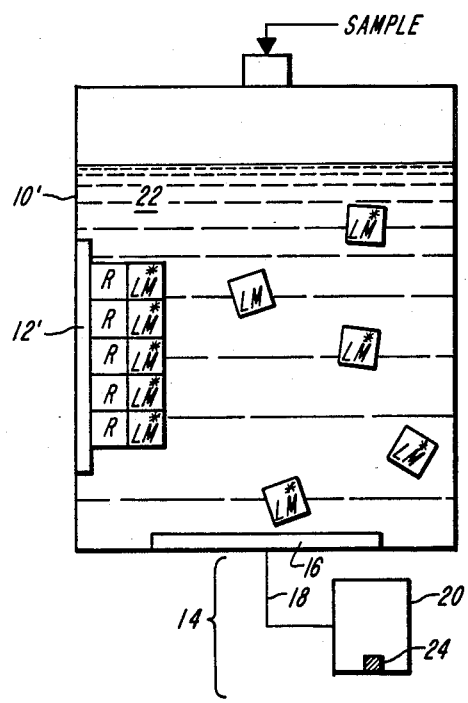
FIG. 3 illustrates apparatus identical to that of FIG. 1 at $t_o$ except the ligand molecules LM are the immobilized species while the receptor molecules R* constitute the labelled free species.
Figure 4:
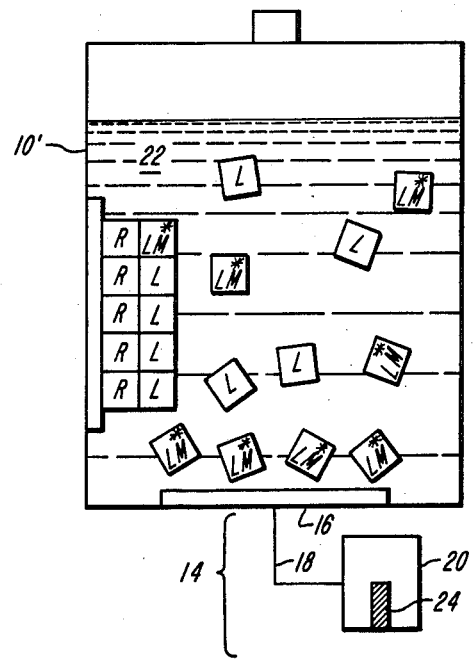
FIG. 4 illustrates the same system as FIG. 3 at time $t_2$.

FIGS. 3, 4, 7, and 8 have a chamber 10' substantially similar to that illustrated in FIGS. 1, 2, 5, and 6, except the immobilized species is bound to a wall 12' displaced from surface 16 by distance greater than the quenching distance D of the beta particles in solution 22. In FIGS. 3 and 4, the receptor molecules R constitute the immobilized species and the ligand molecules LM* form the labelled free species. Before introduction of the sample (FIG. 3), a significant portion of the ligand molecules LM* are bound to the receptor molecules R causing reading 24 to be low since few labeled ligand molecules LM* are within distance D of fluorescent surface 16. Upon introduction of the sample (FIG. 4), ligand L displaces a portion of ligand molecules LM* are bound to receptor molecules R and reading 24 is low. Introduction of ligand L strips LM* molecules from the binding sites of receptor molecules R, and the concentration of ligand molecules LM* in solution increases. The increase in concentration of LM* in solution causes diffusion of ligand molecules LM* about chamber 10' and more labelled ligand molecules LM* enter the region within quenching distance D of fluorescent surface 16. Since more ligand molecules LM* are within the area where the emitted beta particles are not quenched, the number of beta particles incident on fluorescent surface 16 increases, causing reading 24 to increase.

Figure 7:
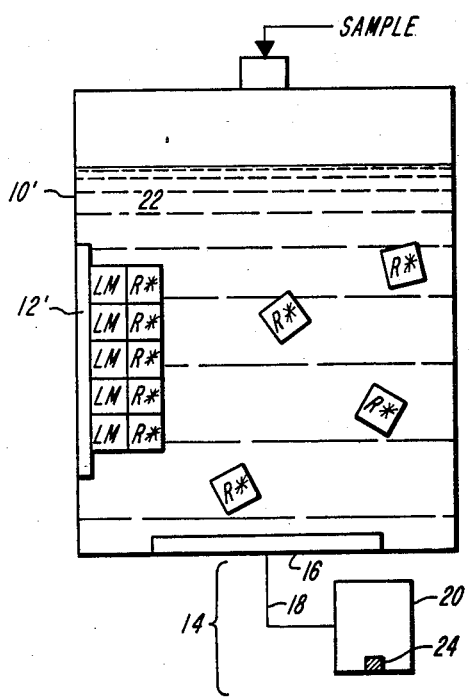
FIG. 7 illustrates apparatus identical to FIG. 3 at time $t_0$ except the ligand molecules LM are immobilized at a distance greater than D from the beta particle detector.
Figure 8:
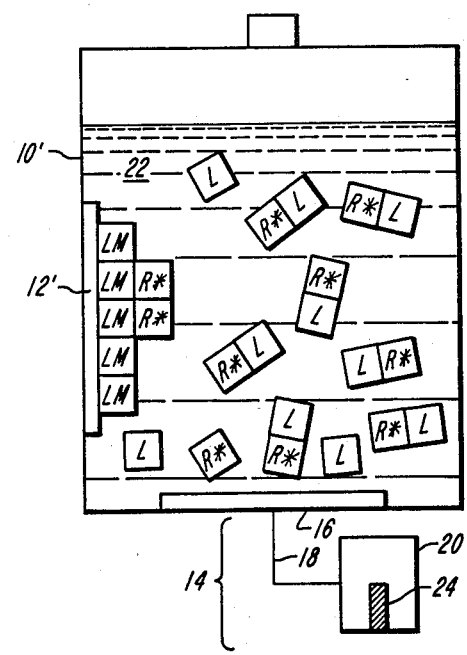
FIG. 8 illustrates the same system as FIG. 7 at time $t_2$.

FIGS. 7 and 8 illustrate exactly the same situation as FIGS. 5 and 6 except the ligand molecules LM constitute the immobilized species and the receptor molecules R* form the labelled free species. The addition of ligand L to the solution (FIG. 8) strips a portion of the labelled receptor molecules R* from the immobilized ligand molecules LM and a portion of the R*/L pairs diffuse to within the quenching distance D of surface 16. Therefore, a larger portion of the beta particles emitted from labelled free species R* are incident on surface 16 and reading 24 increases indicating an increase in ligand L concentration.

In all of the cases previously described, the preferred ligand L is an antigen and preferred receptor molecule is an antibody. The most preferred means of introducing the ligand into the chamber, that is, the preferred input port 26, is a membrane permeable to the ligand but substantially impermeable to the free species. The ligand molecules can either be ligand, a ligand-macromolecule complex or a distinct, cross-reacting species. If the receptor molecules constitute the immobilized species, the preferred ligand molecules are a ligand-macromolecule complex, with either the ligand itself or the macromolecule tagged with the radioactive atom.

Figure 9:
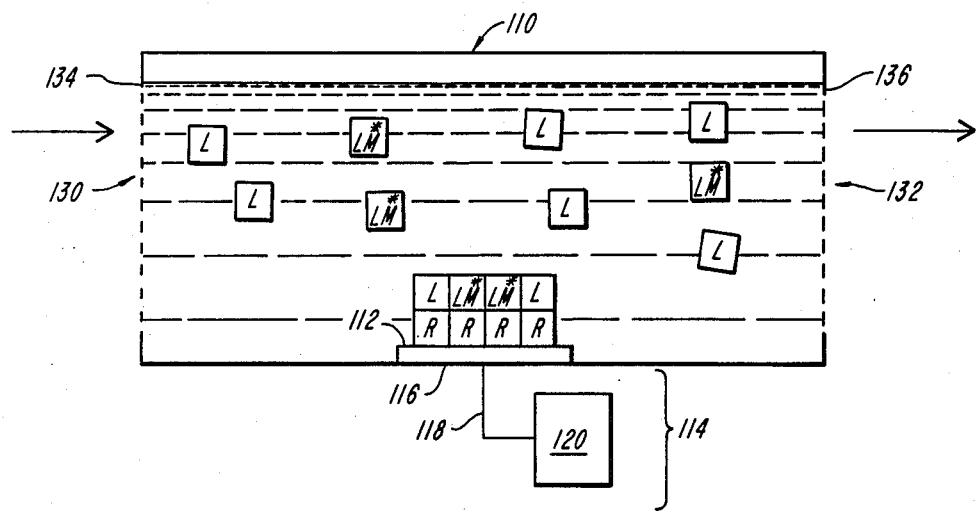
FIG. 9 is a schematic drawing of a preferred embodiment of the invention, a chamber having two semipermeable membranes, the apparatus adapted for continuous assay of ligand concentration in a fluid stream.

FIG. 9 illustrates a most preferred embodiment of the invention, an implantable chamber useful for continuous in vivo assay of ligand level. Chamber 110 has semipermeable membranes 130 and 132 forming portions of walls 134 and 136 respectively. Membranes 130 and 132 are permeable to ligand L and substantially impermeable to the labelled ligand molecules LM*. Receptor molecules R are immobilized on wall 112. Beta particle detector 114 includes fluorescent surface 116, optical fiber 118 and scintillation counter 120. FIG. 9 illustrates a preferred embodiment whereby fluorescent surface 116 is adjacent to wall 112 and emits light in response to incident beta particles. Optical fiber 118 carries the light impulses from surface 116 to scintillation counter 120, producing a reading 124.

In this embodiment, ligand L in solution flows through membrane 130 and reacts with receptor molecules R, displacing ligand molecules LM*. Displaced ligand molecules LM* diffuse away from surface 116 thereby decreasing the number of beta particles incident on surface 116 and, consequently, decreasing reading 124. Since any change in the concentration of ligand L is reflected in the proportion of ligand molecules LM* bound to receptor molecules R and, therefore, reading 124, this apparatus is adapted for continuous assay of ligand concentration. Aqueous solution 122 quenches beta particles emitted from ligand molecules which are about 1 mm from surface 116 (see Table I), so the apparatus can be miniturized and implanted in animal body, e.g., using a catheter. Labelling of the free species with either tritium or carbon-14 is possible.

Unreacted ligand L flows through chamber 110 and exits through membrane 132. Since the amount of ligand L which actually reacts with receptor molecules R is relatively small, the assay will not seriously effect the total concentration of ligand L in the animal body. This property of the assay allows the use of the apparatus for detection of drugs or other ligands or antigens in an animal body without removing a significant portion of the ligand from the fluid stream.

The preferred method of determining the concentration of ligand in the sample is by comparing the output reading from the beta particle detector with a standard curve. The standard curve is often prepared by serial dilution of known ligand solutions and plotting the bound/zero reading ratios versus the log of concentration of the ligand. The standard curve will normally be the familiar sigmoidal shape common to other radioassays, e.g., RIAs. The use of a standard curve permits quick determination of ligand concentration.

As previously stated, the high specificity of the immune reaction makes the antigen/antibody pair the preferred ligand/receptor for use in this process and apparatus. However, any other pair having high specificity may be used. Those skilled in the art will appreciate that other variations of the process and apparatus described herein are useful for practice of the invention. Such other variations are incurred within the following claims.

What is claimed is:

1. A radioassay process for detecting the presence of a ligand in a sample, said process comprising the steps of:
   A. providing a chamber and an associated sensor means for generating a signal representative of the number of beta particles emitted by radioactive atoms incident thereon, said chamber containing:
   (i) a plurality of receptor molecules capable of coupling with said ligand;
   (ii) a plurality of ligand molecules capable of coupling with said receptor molecules, at least one of said pluralities of receptor molecules and ligand molecules being a species immobilized on a solid support within said chamber, the other of said pluralities of receptor molecules and ligand molecules comprising free species labeled with radioactive atoms which emit beta particles;
   (iii) a chamber medium; and
   (iv) means for fixing the position of said sensor means with respect to said support;
   B. introducing a solution containing said sample within said chamber, said solution and said chamber medium comprising a quenching solution adapted to quench substantially all beta particles emitted by said radioactive atoms before said particles travel a predetermined quenching distance D;
   C. allowing ligand in said sample and ligand molecules to compete for sites of attachment on said receptor molecules and allowing said free species within said chamber to diffuse about said solution;
   D. detecting said signal generated by said sensor means while said solution and said free species remain within said chamber, said signal being representative of the number of said radioactive atoms located within said quenching distance D of said sensor means; and
   E. comparing said signal with a base value to detect the presence of ligand in said sample.

2. The process of claim 1 wherein said plurality of receptor molecules are immobilized on said solid support at a location within a distance D of said sensor means, said ligand molecules are labeled with said radioactive atoms, and during step C, a portion of said ligand molecules diffuses away from said immobilized receptor molecules whereby at least a portion of the beta particles emitted by said radioactive atoms are quenched by said solution before reaching said sensor means, the concentration of ligand in said sample is a monotonically decreasing function of said signal.

3. The process of claim 1 wherein said plurality of receptor molecules are immobilized on said solid support at a location in said chamber spaced apart from said sensor means by a distance greater than D, said ligand molecules are labeled with said radioactive atoms, and during step C, a portion of said ligand molecules diffuses away from said immobilized receptor molecules to a location less than a distance D from said sensor means whereby at least a portion of said beta particles emitted by said radioactive atoms in said portion of ligand molecules are detected by said sensor means, the concentration of said ligand in said sample is a monotonically increasing function of said signal.

4. The process of claim 1 wherein said plurality of ligand molecules are immobilized on said solid support at a location within a distance D of said sensor means, said receptor molecules are labeled with said radioactive atoms, and during step C, a portion of said plurality of receptor molecules diffuses away from said immobilized ligand molecules whereby at least a portion of the beta particles emitted by said radioactive atoms are quenched by said solution before reaching said sensor, and the concentration of ligand in said sample is a monotonically decreasing function of said signal.

5. The process of claim 1 wherein said plurality of ligand molecules are immobilized on said solid support at a location in said chamber spaced apart from said sensor means by a distance greater than D, said receptor molecules are labeled said radioactive atoms, and during step C, a portion of said plurality receptor molecules diffuses away from said immobilized ligand molecules to a location less than D from said sensor means whereby at least some of the beta particles emitted by said radioactive atoms are incident on said sensor means, the concentration of said ligand is a monotonically increasing function of said signal.

6. The process of claim 1 wherein said chamber further comprises a membrane permeable to said ligand and substantially impermeable to said free species.

7. The process of claim 6 wherein said free species comprises said ligand molecules coupled with radioactively tagged macromolecules.

8. The process of claim 6 wherein said process is a continuous process for detecting ligand.

9. The process of claim 6 wherein said process comprises the additional step of implanting said chamber within an animal body and allowing a fluid in said animal body comprising said sample to traverse said membrane.

10. The process of claim 1 wherein said solid support comprises a wall of said chamber.

11. The process of claim 1 wherein said quenching solution is an aqueous solution.

12. The process of claim 1 wherein said sensor means comprises a surface comprising a material which fluoresces in response to incident beta particles.

13. The process of claim 12 further comprising means communicating with said surface for detecting fluorescent events at said surface.

14. The process of claim 12 wherein said fluorescent material is coated on a first wall of said chamber.

15. The process of claim 14 wherein said solid support comprises said first wall.

16. The process of claim 1 wherein a portion of said ligand molecules react with said receptor molecules before the introduction of said sample into said chamber.

17. The process of claim 1 wherein said ligand comprises an antigen and said receptor molecule comprises an antibody.

18. The process of claim 4 wherein said ligand molecules comprise ligand.

19. The process of claim 5 wherein said ligand molecules comprise ligand.

20. Apparatus for detecting the presence of a ligand in a sample, said apparatus comprising:
a reaction chamber containing a plurality of ligand molecules and a plurality of receptor molecules capable of coupling with said ligand and said ligand molecules, one of said plurality of receptor molecules and said plurality of ligand molecules being a species immobilized on a solid support disposed within said chamber, the other comprising a free species labeled with radioactive atoms which emit beta particles;
a solution within said chamber capable of quenching beta particles before said particles travel a distance D within said solution;
associated sensor means responsive to incident beta particles emitted from the radioactive atoms of said free species disposed within the region of said chamber which is less than said distance D from said sensor; and
means for introducing said sample into said chamber.

21. The apparatus of claim 20 for continuous detection of said ligand wherein said means for introducing comprises a membrane permeable to said ligand in said sample and substantially impermeable to said ligand molecules.

22. The apparatus of claim 21 wherein said free species comprises said plurality of ligand molecules and said plurality of ligand molecules comprise radioactively tagged macromolecules.

23. The apparatus of claim 20 wherein said sample comprises a portion of said solution.

24. The apparatus of claim 20 wherein said associated sensor means comprises a surface comprising a material which fluoresces in response to beta particles.

25. The apparatus of claim 24 further comprising means communicating with said surface for detecting fluorescent events at said surface.

26. The apparatus of claim 25 wherein said fluorescent material is coated on a first wall of said chamber.

27. The apparatus of claim 26 wherein said solid support comprises said first wall.

28. The apparatus of claim 25 wherein said means for detecting fluorescence comprises a scintillation counter.

29. The apparatus of claim 21 wherein said apparatus is adapted for in vivo detection of said ligand and comprises an implantable chamber and means for delivering an output signal from said associated sensor means.

30. The apparatus of claim 20 wherein said receptor molecules comprise said free species and said ligand molecules comprise ligand.

31. Apparatus for continuous assay of a ligand in an aqueous sample, said apparatus comprising:
a chamber;
a solid support adapted for immobilizing a member selected from the group consisting of a plurality of ligand molecules and a plurality of receptor molecules capable of reversibly binding with said ligand and said ligand molecules, said solid support being disposed within said chamber at a first location;
a beta particle detector in communication with said chamber at a second location, said detector comprising means for delivering to the exterior of said chamber a signal indicative of the number of beta particles detected by said detector; and
means for introducing an aqueous sample into said chamber, said aqueous sample comprising a solution capable of quenching a beta particle before said beta particle travels a distance D in said solution.

32. The apparatus of claim 31 wherein said first location is less than a distance D from said second location.

33. The apparatus of claim 31 wherein said first location is spaced apart from said second location by a distance greater than D.

34. The apparatus of claim 31 wherein said beta particle detector comprises a surface comprising a material which fluoresces in response to incident beta particles.

35. The apparatus of claim 31 wherein said means for introducing comprises a semipermeable membrane permeable to ligand contained in said sample and substantially impermeable to ligand molecules contained within said chamber.

36. The apparatus of claim 35 wherein said membrane is disposed to form a portion of a wall of said chamber.

37. The apparatus of claim 34 wherein said means for communicating comprises an optical fiber.

38. The apparatus of claim 31 further comprising a scintillation counter connected to said means for communicating and exterior to said chamber.

* * * * *